United States Patent [19]
Pick et al.

[11] 4,167,186
[45] Sep. 11, 1979

[54] SYRINGE, SUCH AS A VAGINAL DOUCHE, AND CANNULA THEREOF

[75] Inventors: Ernest W. Pick, Cos Cob; Joseph M. Denaro, Stamford; Henry R. Goerke, Norwalk, all of Conn.

[73] Assignee: The Purdue Frederick Company, New York, N.Y.

[21] Appl. No.: 831,595

[22] Filed: Sep. 8, 1977

[51] Int. Cl.$^2$ ............................................. A61M 1/00
[52] U.S. Cl. ..................................... 128/232; 128/251
[58] Field of Search ................ 128/232, 224, 251, 239

[56] References Cited

U.S. PATENT DOCUMENTS

| | | | |
|---|---|---|---|
| 758,673 | 5/1904 | Meinecke | 128/232 |
| 766,106 | 7/1904 | Foote | 128/232 |
| 2,333,383 | 11/1943 | Klarchuk | 128/239 |
| 3,968,797 | 7/1976 | Packer et al. | 128/232 |
| 4,057,060 | 11/1977 | Roth | 128/232 |

FOREIGN PATENT DOCUMENTS

| | | | |
|---|---|---|---|
| 1575513 | 7/1969 | France | 128/239 |
| 439393 | 9/1948 | Italy | 128/239 |

*Primary Examiner*—John D. Yasko
*Attorney, Agent, or Firm*—Steinberg & Blake

[57] ABSTRACT

A syringe, particularly a vaginal douche, has a cannula consisting of an elongated hollow tubular body having one open end and an opposed transverse end wall formed with an opening through which a central axis of the cannula body extends. The cannula body has substantially midway between its ends a transverse minimum cross section while tapering only slightly from the transverse end wall toward the minimum cross section. Between its open end and its minimum cross section the cannula body tapers to a substantially greater degree and has the configuration of part of a hollow cone. At its exterior between its minimum cross section and transverse end wall the cannula body is formed with grooves uniformly distributed about the central axis of the cannula body and separated from each other by ribs. Adjacent but inwardly of these ribs the cannula body is formed with additional openings passing therethrough so that a liquid can discharge through the cannula openings. At its open end the cannula is internally threaded for attachment to a squeeze bottle.

5 Claims, 9 Drawing Figures

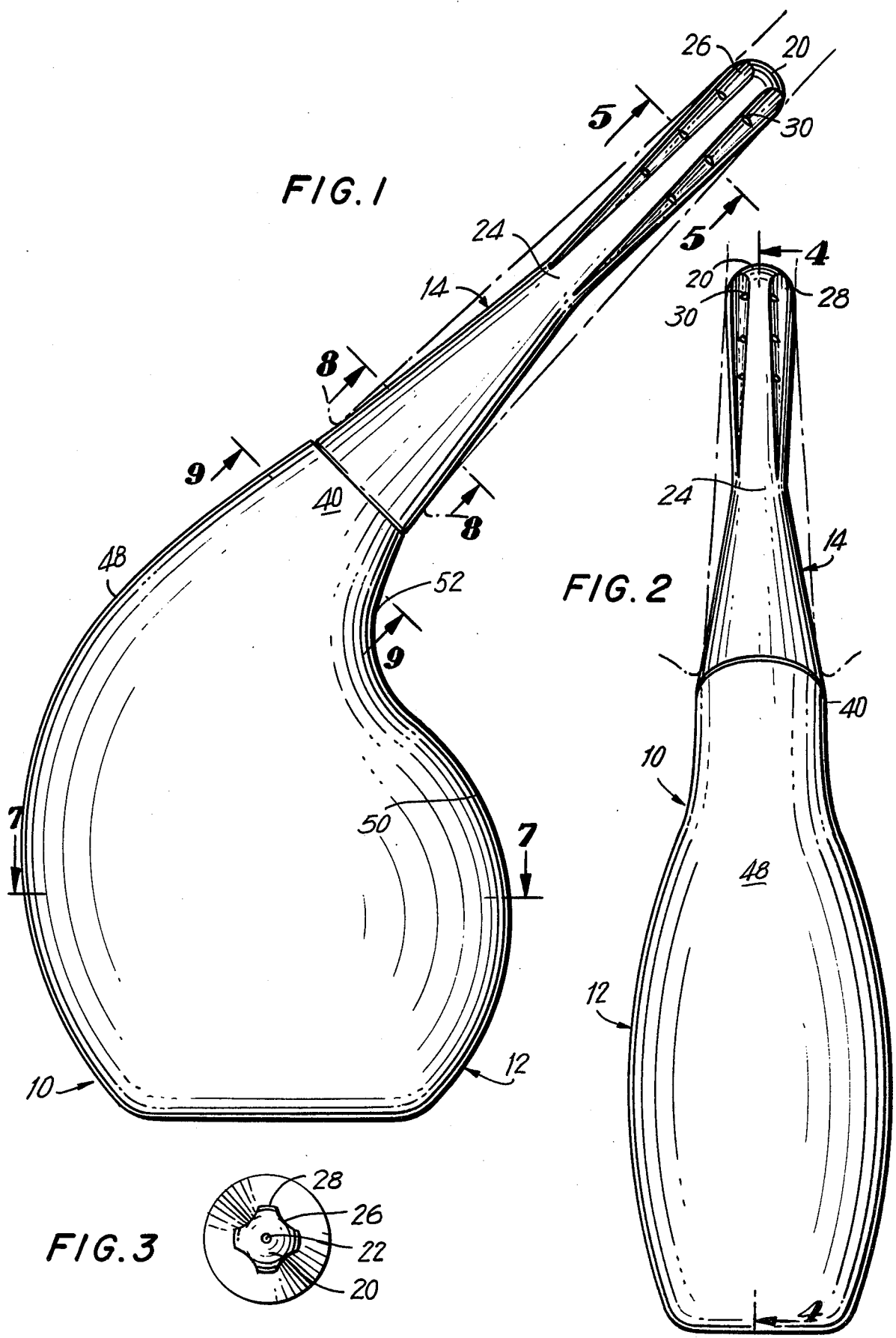

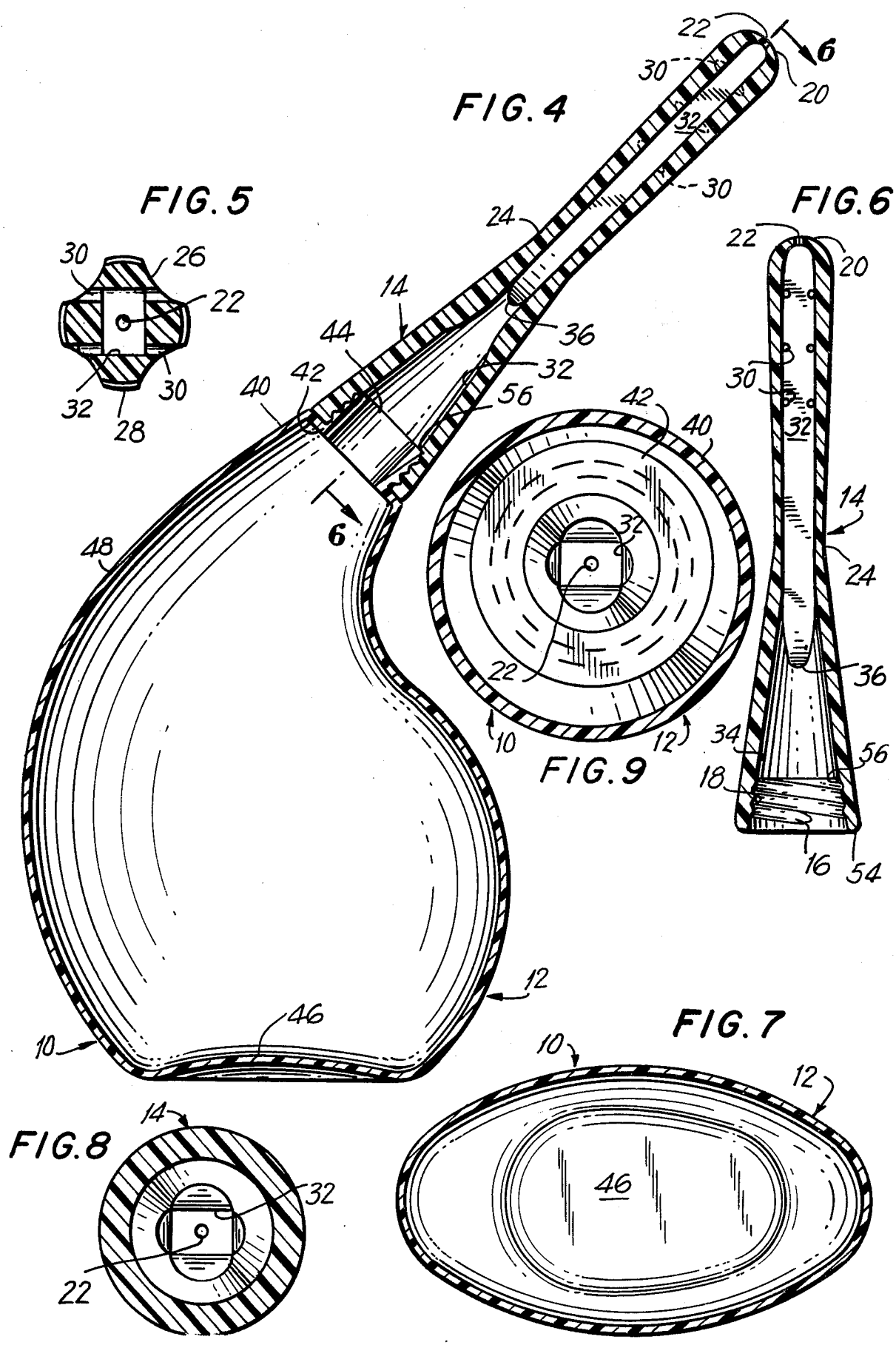

SYRINGE, SUCH AS A VAGINAL DOUCHE, AND CANNULA THEREOF

BACKGROUND OF THE INVENTION

The present invenion relates to syringes.

In particular, the present invention relates to a syringe which is adapted to be used as a vaginal douche.

Structures of the above type are of course well known. They generally include a squeeze bottle to which there is removably connected an elongated hollow cannula formed distant from the squeeze bottle with openings through which the contents of the squeeze bottle can be discharged.

Conventional syringes of the above general type, particularly when used as a vaginal douche, suffer from serious drawbacks. Thus, when the cannula of such a syringe is inserted into the vagina, the internal tissue lining the vagina comes into close contact with the exterior surface of the cannula. When the squeeze bottle is compressed to discharge liquid through the openings of the cannula, this liquid washes the interior of the vagina which thereafter comes again into close contact with the exterior surface of the cannula. Immediately thereafter the squeeze bottle is released so that it expands, creating a suction at the exterior of the cannula, and because of the configuration of the exterior surface of a conventional cannula this suction results in undesirable pressure of the inner vaginal lining tissue against the exterior surface of the cannula. The sucking of the internal vaginal tissue against the exterior surface of the cannula creates not only considerable difficulty in removing the cannula from the vagina but also results often in injury to the tender inner vaginal tissue as well as damage to the protective viscous layer of mucosa and the like situated at the interior of the vagina. As a result of these drawbacks conventional syringes designed to be used for the purpose of vaginal douching are not as widely used as would otherwise be the case and when used must be manipulated with great care and at best afford the possibility of vaginal douching only with considerable discomfort.

SUMMARY OF THE INVENTION

It is accordingly a primary object of the present invention to provide a syringe of the above general type which will avoid the above drawbacks.

Thus, it is a primary object of the present invention to provide for a syringe a cannula which is constructed in such a way that there will be no possibility of damage or injury to the vaginal tissue or protective lining thereof.

It is furthermore an object of the present invention to provide a cannula of this type which is simple and inexpensive while at the same time being highly effective for its intended purpose.

In addition it is an object of the present invention to combine with such a cannula a squeeze bottle which is particularly effective in combination with the cannula of the invention.

Yet another object of the present invention is to provide a construction of the above type which is simple and inexpensive while at the same time being made of materials which can be used repeatedly under the most hygienic conditions.

According to the invention the syringe which is to be used as a vaginal douche includes a cannula consisting of an elongated hollow tubular body having one open end and opposite therefrom a transverse end wall formed with a central opening through which a central axis of the tubular cannula body extends. Substantially midway between its ends the cannula body has a minimum transverse cross section with the cannula body tapering only slightly from its transverse end wall toward its minimum cross section. The open end of the cannula body is substantially larger than the transverse end wall thereof and between its open end and its minimum cross section the cannula body gradually tapers and has the configuration of part of a hollow cone, the open end of the tubular cannula body having a means such as threads for removably connecting the cannula to a squeeze bottle. Between its minimum cross section and transverse end wall the cannula body is formed at its exterior with a plurality of longitudinally extending grooves which are uniformly distributed about the axis of the cannula body and which are separated from each other by ribs, with the cannula body being formed with additional openings situated inwardly of but adjacent these ribs.

BRIEF DESCRIPTION OF DRAWINGS

The invention is illustrated by way of example in the accompanying drawings which form part of this application and in which:

FIG. 1 is a side elevation of a syringe according to the invention;

FIG. 2 is an end elevation of the syringe of FIG. 1 as seen from the left of FIG. 1;

FIG. 3 is an end view of the cannula of FIG. 1 as seen from the upper right of FIG. 1;

FIG. 4 is a sectional elevation of the syringe of FIGS. 1 and 2, taken along line 4—4 of FIG. 2 in the direction of the arrows;

FIG. 5 is a transverse sectional illustration of the cannula taken along line 5—5 of FIG. 1 in the direction of the arrows;

FIG. 6 is a longitudinal sectional elevation of the cannula taken along line 6—6 of FIG. 4 with the part of the squeeze bottle which is connected to the cannula being omitted from FIG. 6;

FIG. 7 is a sectional plan view of the squeeze bottle taken along line 7—7 of FIG. 1 in the direction of the arrows;

FIG. 8 is a transverse section of the cannula of FIG. 1 taken along line 8—8 of FIG. 1 in the direction of the arrows; and FIG. 9 is a transverse section of part of the squeeze bottle of FIG. 1 taken along line 9—9 of FIG. 1 in the direction of the arrows.

DESCRIPTION OF PREFERRED EMBODIMENTS

Referring now to FIGS. 1 and 2, the syringe 10 of the invention which is illustrated therein, and which is intended to be used as a vaginal douche, is made up of two components, namely, a squeeze bottle 12 and a cannula 14. These components may be made of any suitable plastic material such as, for example, polyethylene or polypropylene.

As is apparent particularly from FIGS. 4 and 6, the cannula 14 is in the form of an elongated tubular body having an open end 16 formed with internal threads 18 which form a means for removably attaching the cannula 14 to the squeeze bottle 12. Opposite to its open end 16 the cannula body has a transverse end wall 20 formed with a central opening 22 through which the central axis of the cannula body extends.

Between its transverse end wall 20 and its open end 16 the elongated cannula has a portion 24 which is of a minimum cross section in a plane normal to the central axis of the cannula body. It will be seen from the drawing that this minimum cross section 24 of the cannula body is situated substantially midway between its opposed ends. Moreover, the transverse cross section of the cannula at its open end 16 is substantially larger than its cross section at its end wall 20. The cannula body at its exterior tapers only slightly from the transverse end wall 20 toward the minimum cross section 24, while the extent of taper from the open end 16 to the minimum cross section 24 is substantially greater. Between its open end 16 and minimum cross section 24 the cannula 14 has the configuration of part of a hollow cone.

Between the minimum cross section 24 and the transverse end wall 20, which has an exterior rounded convex surface, the cannula body is formed with a plurality of elongated longitudinally extending grooves 26 uniformly distributed about the central axis of the cannula, FIG. 3 illustrating that there are in the example illustrated four such grooves 26. These grooves are separated from each other by ribs 28 which have exterior convex rounded surfaces merging into the concave surfaces of the grooves 26. These grooves 26 start at the region of the minimum cross section 24 and become gradually wider as they approach the end wall 20, and the transverse dimension of the cannula body between the innermost portions of a pair of opposed grooves 26 thereof is no greater than the transverse dimension of the cannula body at the minimum cross section 24 thereof. Thus it will be seen that with this construction there are two pairs of diametrically opposed ribs separated from each other by two pairs of diametrically opposed grooves.

In addition to being formed with the central opening 22 at the transverse wall 20 the cannula body 14 is also formed with a plurality of openings 30 three of which are situated in each groove 26 in the illustrated example. These openings are equidistant from each other and arranged as illustrated longitudinally of the cannula 14. However, it will be seen that the openings 30 are all located only in the region of one of the pairs of opposed ribs 28. Thus, as is shown most clearly in FIG. 5, the openings 30 are only located adjacent the pair of horizontal ribs 28 of FIG. 5.

It will be seen from FIG. 5 that the horizontal pair of diametrically opposed ribs 28 have, as viewed in FIG. 5, upper and lower side edges situated in a pair parallel planes normal to the plane of FIG. 5 and situated equidistantly from the central axis of the cannula, this latter central axis also being normal to the plane of FIG. 5. The openings 30 are situated only in this pair of parallel planes which contain the side edges of the horizontal pair of diametrically opposed ribs of FIG. 5.

As a result of this feature, the liquid which is discharged through the openings 30 will only discharge in a pair of mutually opposed directions while enabling the vertical pair of diametrically opposed ribs 28 of FIG. 5 to serve to maintain the inner surface of the vagina away from any openings such as the openings 30. Moreover, since these openings 30 are situated only inwardly of the outer convex surfaces of the diametrically pair of opposed horizontal ribs of FIG. 5, these openings 30 also are spaced inwardly from the inner surface of the vagina at the region of the horizontal pair of ribs 28 of FIG. 5.

In addition, when the cannula of the invention is manufactured, it is molded between a pair of mold halves which can conveniently have the pins around which the openings 30 are formed, and these pins need only be located in a pair of planes to provide the construction of the invention, so that certain manufacturing advantages are also achieved by way of the structure in connection with the openings 30.

As is apparent from FIGS. 4-6, the several ribs 28 are solid. Thus, the interior of the cannula at its portion extending from the minimum cross section 24 to the transverse end wall 20 is not of a circular cross section. Rather, this interior portion of the cannula is defined by flat surfaces which intersect each other so as to provide the hollow interior of the cannula between the minimum cross section portion 24 and the end wall 20 with a polygonal cross section which in the illustrated example is rectangular. Thus, this hollow interior portion of the cannula is defined by interior flat surfaces 32, and these surfaces 32 merge into the inner tapering conical surface 34 of the portion of the cannula between its open end 16 and minimum cross section 24 at the curved parts 36 indicated in FIGS. 4 and 6. Thus it will be seen that the merging of the flat surfaces 32 into the inner tapered surface 34 of the hollow part of the cannula which forms part of a cone is situated between the open end 16 and the minimum cross section 24. Of course the open end 16 is much greater in cross section than the transverse wall 20 and the extent of taper of the cannula between its open end 16 and minimum cross section 24 is greater than the relatively slight taper between the end wall 20 and the minimum cross section 24.

While the plastic material used for the cannula 14 provides the latter with a certain flexibility at its region between open end 16 and minimum cross section 24, with the cannula actually being easily flexible at the minimum cross section 24, nevertheless the solid ribs 28 resulting from the above construction render the cannula much more rigid between the minimum cross section 24 and the transverse end wall 20. Thus the cannula of the invention does not have hollow ribs which can easily collapse.

As a result of the above features of the cannula 14 of the invention, the cannula can be comfortably and easily inserted into the vagina. Thus the relative rigidity of the leading end of the cannula between its wall 20 and minimum cross section 24 enables the cannula to be comfortably introduced into the vagina. At the same time the pair of diametrically opposed ribs 28 which are arranged vertically in FIG. 5 serve, as pointed out above, to contribute to holding the inner surface of the vagina away from the openings 30, and this result is also contributed to by way of the horizontal ribs 28 of FIG. 5, as pointed out above. In addition, because of the minimum cross section 24, the inner surface of the vagina will extend as indicated by the phantom lines in FIGS. 1 and 2. In other words the relatively large cross section of the tapered portion of the cannula between its open end 16 and minimum cross section 24 and the cross section of the end wall 20 which is larger than minimum cross section 24 will serve to dispose the inner surface of the vagina in such a way that it will tend to remain spaced away from the exterior surface of the cannula. This is in sharp contrast with conventional cannulas which, for example, gradually taper all the way from the open end to the front tip where the cannula is closed, for example. Thus, because of the minimum cross section 24, when, after squeezing the bottle 12 to discharge liquid through the cannula openings, the bottle 12 is released to expand, the suction will not succeed in pulling the inner vaginal surface against the cannula because of the manner in which this inner vaginal surface is maintained away from the cannula by the above-described structure, and of course the relatively rigid ribs 28 also contribute to this result, particularly in combination with the particular arrangement of the openings 30. It has been found from tests carried out with the structure of the invention that there will in fact be no tendency for the inner surface of the vagina to stick undesirably to the exterior surface of the cannula due to any suction created when the squeeze bottle expands.

The squeeze bottle 12 has in the region of the open end 16 of the cannula 14 an open end portion 40 which is of a circular cross section, as indicated in FIG. 9. This portion 40 has an inner shoulder 42 beyond which the portion 40 has an exteriorly threaded neck 44 which can be threaded into the thread 18 at the open end portion 16 of the cannula 14. Thus through this construction it is possible to removably connect the cannula and squeeze bottle to each other. Moreover, the exterior surface of the portion 40 of the squeeze bottle 12 tapers in such a way as to form a continuation of the taper of the portion of the cannula extending between its open end 16 and the minimum cross section 24. As may be seen from FIG. 8, this portion of the cannula is also of a circular cross section, so that the conical tapering of the cannula at the region of its opening 16 continues with substantially no interruption along the portion 40 of the squeeze bottle. Thus this portion 40 may, if necessary, be considered as and will function as an operative extension of the cannula.

Distant from its open end 40 of circular cross section the squeeze bottle 12 has a flat bottom wall 46 which is of an elliptical cross section, as shown most clearly in FIG. 7. The ellipse defined by the edge of the bottom wall 46 has a major axis which together with the central axis of the cannula are situated in a plane of symmetry of the squeeze bottle 12. This plane of symmetry is the plane of the section of FIG. 4 and is of course situated along the line 4—4 of FIG. 2.

As is apparent from FIGS. 2 and 7 while this squeeze bottle bulges between its bottom wall 46 and upper open end region 40, at the same time between the open end region 40 and the flat bottom wall 46 the squeeze bottle has in any plane parallel to the wall 46 and normal to the plane of symmetry an elliptical cross section, as is apparent from FIG. 7 in particular.

In its plane of symmetry the squeeze bottle terminates along one side in a convexly curved edge 48 which continues without interruption as an extension of the cannula all around to the bottom wall 46. At its opposite side edge the squeeze bottle 12 also has a convex curvature 50, but at this opposite side the convexly curved edge 50 merges into a concavely curved edge region 52 which joins the circular portion 40. Thus at its right side edge, as viewed in FIG. 1, the squeeze bottle has a substantially S-shaped configuration.

As is apparent particularly from FIGS. 1 and 4, when the bottom wall 46 of the squeeze bottle is situated in a horizontal plane forming the bottom of the assembly, the cannula 14 has its central axis inclined upwardly away from this horizontal plane at an angle of approximately 45°. In addition, the cannula extends laterally beyond the squeeze bottle, to the right thereof as viewed in FIGS. 1 and 4, through a substantial distance. In fact it will be seen that the minimum cross section 24 of the cannula is situated laterally beyond the squeeze bottle. Nevertheless, the weight distribution of the assembled squeeze bottle and cannula is such that even when the squeeze bottle is empty the structure will remain stably on a horizontal surface engaged by the bottom wall 46.

The above-described relationship between the cannula and squeeze bottle has proved in practice to provide a vaginal douche which is extremely convenient to use in a highly effective manner, without any risk of injury and without any discomfort. The plastic materials, such as polyethylene or polypropylene, which provide the squeeze bottle and cannula with the desired flexibility and resiliency, at the time permit the squeeze bottle and cannula to be readily cleaned in the most hygienic manner. Also, the threaded connection between the cannula and squeeze bottle enable the cannula and squeeze bottle to be very quickly and easily assembled and disassembled. At the same time, by way of this threaded connection it is possible for the circular end surface 54 of the cannula to be pressed tightly against the exterior surface of the shoulder 42 of the squeeze bottle 12, so that in this way fluid-tightness is assured. It is to be noted that the end face of the neck 44 also presses against a shoulder 56 formed in the interior of the cannula to contribute to the fluid tightness, and of course the threads themselves contribute to this fluid-tightness, so that when the structure is used there is no tendency for the contents to be undesirably discharged at the connection between the cannula and squeeze bottle.

While it is of course theoretically possible to use the cannula of the invention with other squeeze bottles, provided the latter have suitable threads which match those of the cannula, nevertheless particular advantages are achieved when the squeeze bottle of the invention is used with the cannula of the invention because of the particular relationship between the cannula and squeeze bottle of the invention, as set forth above.

What is claimed is:

1. A syringe, such as a vaginal douche, comprising a cannula consisting of an elongated hollow tubular body having a central axis and having one open end and distant therefrom an opposed transverse end wall formed with an opening passing therethrough and through which said central axis extends, said cannula body having substantially midway between said open end and transverse end wall thereof a minimum transverse cross section in a plane perpendicular to said axis and said body tapering slightly from said transverse end wall toward said minimum cross section while tapering to a substantially greater extent from said open end toward said minimum cross section, the latter portion of said body between said open end and minimum cross section thereof forming part of a hollow cone, and said body being formed at its exterior between said minimum cross section and transverse wall with a plurality of grooves distributed uniformly about said axis with said body having ribs situated between said grooves and said body being formed inwardly of said ribs between said minimum cross section and transverse wall thereof with a plurality of openings through which a liquid in the hollow interior of said body can discharge with the liquid also being capable of discharging through said central opening of said end wall of said body, and a squeeze bottle removably connected with said cannula body at said open end thereof, said squeeze bottle having next to said cannula body an open end region which tapers in the same way as said body at the region of said open end thereof and forms an extension of said open end of said body, said squeeze bottle having distant from said open end region thereof a flat end wall of substantially elliptical configuration having a major axis, said squeeze bottle having a plane of symmetry which contains said major axis as well as said central axis of said cannula body and said squeeze bottle also having in any plane parallel to said flat end wall of said squeeze bottle and normal to said plane of symmetry while being situated between said open end region of said bottle and said flat end wall thereof also an elliptical cross section having a major axis situated in said plane of symmetry, said squeeze bottle terminating in said plane of symmetry along one side in a convexly curved edge region extending from said open end region of said bottle to said flat end wall of said bottle and forming a continuation of said open end region of said bottle and on the opposite side terminating also in a convexly curved edge region which, however, at the open end region of said bottle merges into a concave edge portion which together with said convexly curved portion at said opposite side of said squeeze bottle provides the latter with a substantially S-shaped curvature.

2. The combination of claim 1 and wherein when said flat end wall of said squeeze bottle is situated in a bottom horizontal plane, said central axis of said cannula body is inclined upwardly from the latter horizontal plane at an angle of approximately 45°.

3. The combination of claim 2 and wherein said cannula body projects through a substantial distance laterally beyond said substantially S-shaped edge of said squeeze bottle.

4. The combination of claim 3 and wherein said minimum cross section of said cannula body is situated laterally beyond said substantially S-shaped edge of said squeeze bottle.

5. The combination of claim 1 and wherein said cannula body and squeeze bottle have internal and external threads, respectively, for removably connecting them to each other.

* * * * *